United States Patent [19]

Marvola et al.

[11] Patent Number: 4,599,326
[45] Date of Patent: Jul. 8, 1986

[54] ACETYL ERYTHROMYCIN STEARATE, AND COMPOSITIONS CONTAINING IT

[75] Inventors: Martti L. A. Marvola; Esko V. Marttila, both of Helsinki; Jaakko A. Uotila; Aino K. Pippuri, both of Espoo; Pekka J. Kairisalo, Helsinki; Erkki J. Honkanen, Vantaa, all of Finland

[73] Assignee: Orion-yhtymä Oy, Espoo, Finland

[21] Appl. No.: 686,753

[22] Filed: Dec. 27, 1984

[30] Foreign Application Priority Data

Jan. 6, 1984 [DK] Denmark ................... 58/84

[51] Int. Cl.$^4$ ................. A61K 31/70; C07H 17/08
[52] U.S. Cl. ......................... 514/29; 536/7.2
[58] Field of Search ............ 536/7.1, 7.2, 7.4; 424/180; 514/29

[56] References Cited

U.S. PATENT DOCUMENTS 4,150,220 4/1979 Sciavolino ............... 536/7.2
4,349,545 9/1982 Gouin d'Ambrieres et al. ... 536/7.4

Primary Examiner—Johnnie R. Brown
Assistant Examiner—Elli Peselev
Attorney, Agent, or Firm—Burns, Doane, Swecker & Mathis

[57] ABSTRACT

The invention relates to a new antibiotic compound, acetyl erythromycin stearate having formula I

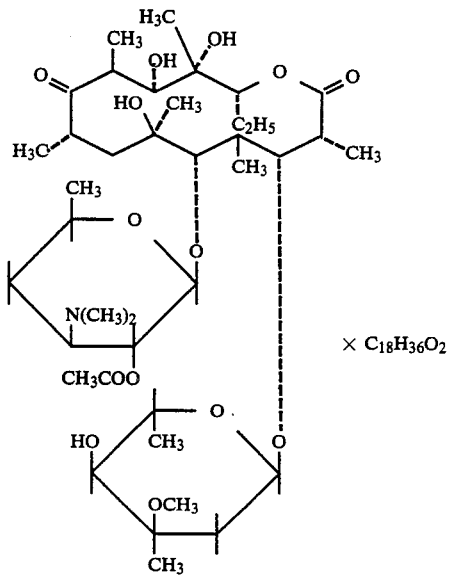

The compound according to the invention is absorbed readily from the alimentary tract. Gastric acid does not convert the compound according to the invention to an uneffective form as is the case with some other erythromycin antibiotics. Absorbing is good also when the patient eats when taking the new medicine.

The compound according to the invention is prepared by reacting erythromycin base with acetyl halide in an organic solvent in the presence of an acid acceptor. The stearate salt is prepared from the obtained ester without in between isolating the ester.

3 Claims, 2 Drawing Figures

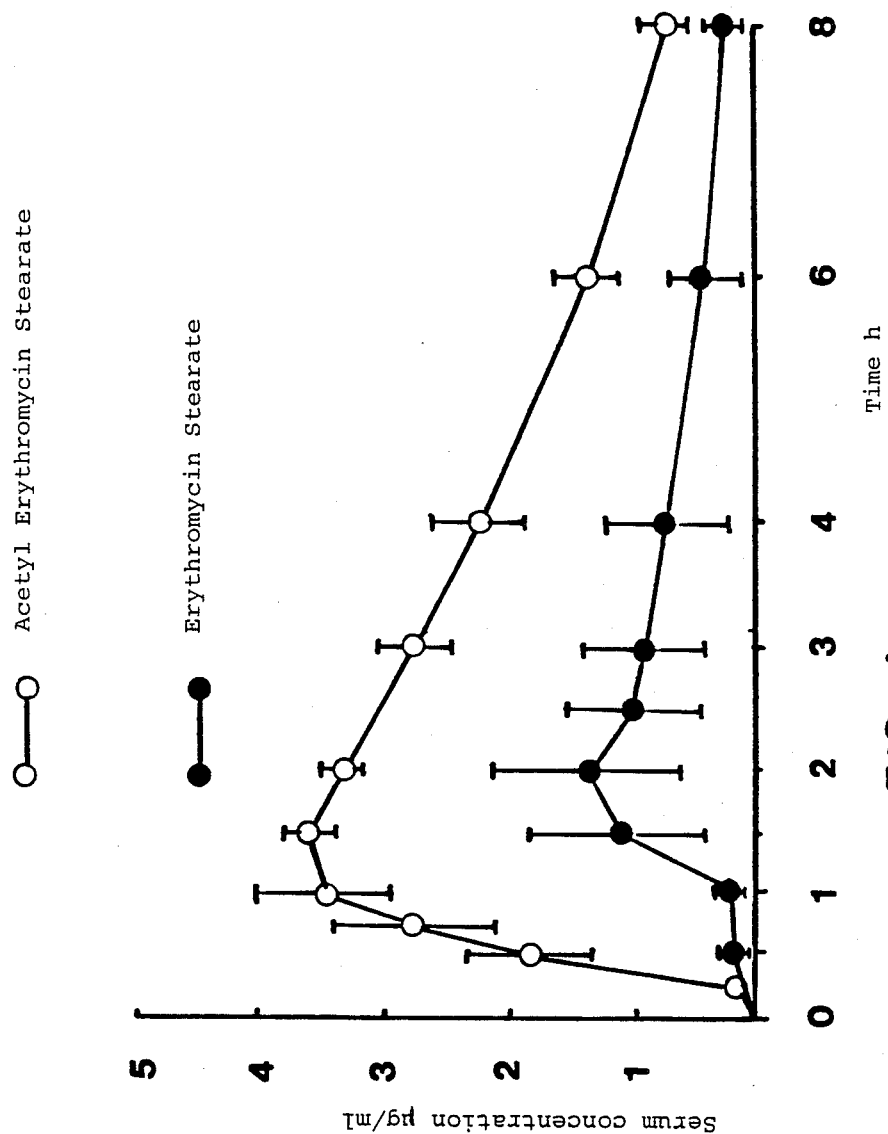

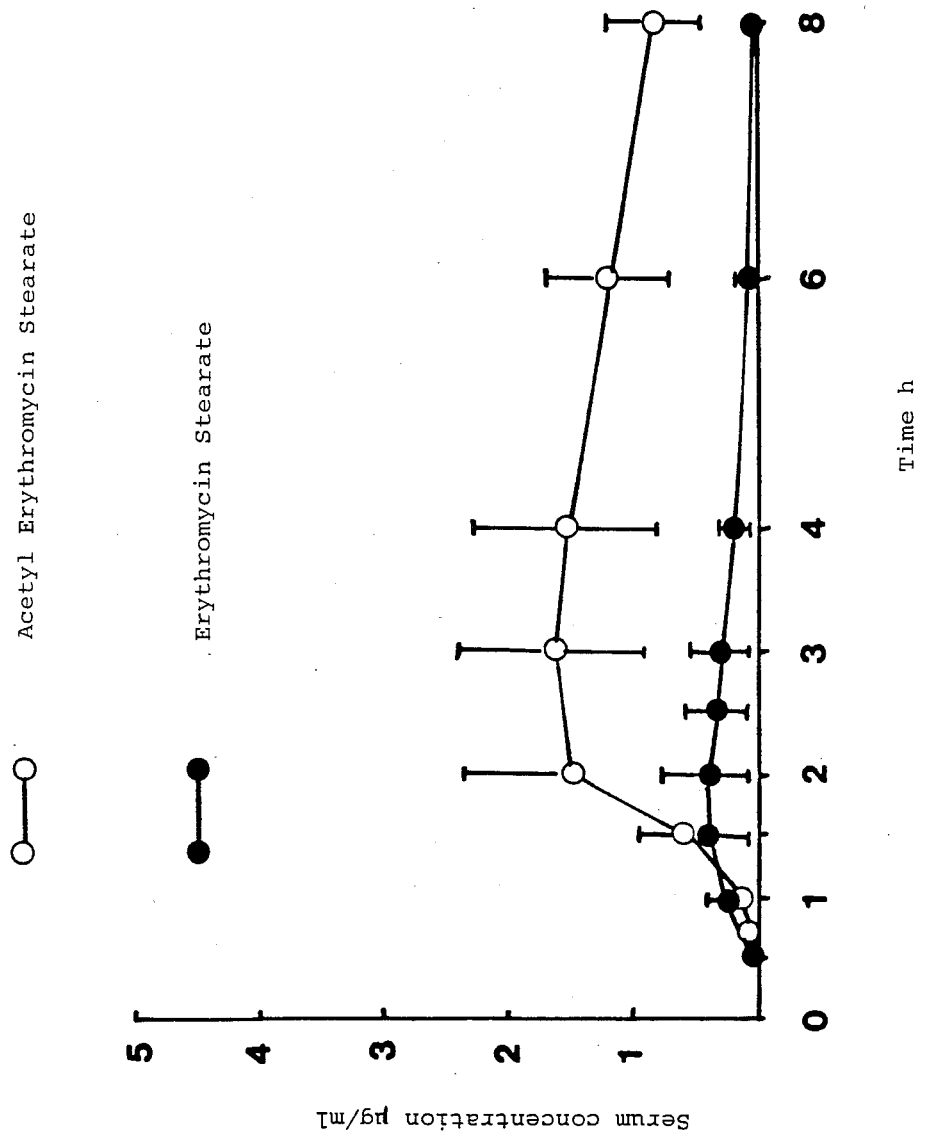

ACETYL ERYTHROMYCIN STEARATE, AND COMPOSITIONS CONTAINING IT

The present invention relates to an antibiotic compound which is novel. The compound is acetyl erythromycin stearate, which has been observed to have advantageous properties as compared with certain known erythromycins and the formula of which is I

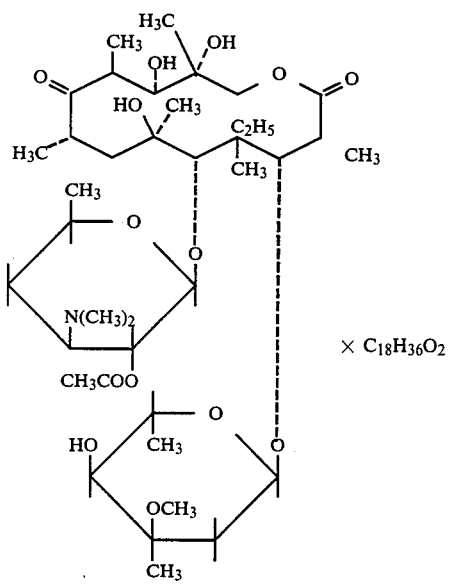

The invention also relates to a method for the preparation of acetyl erythromycin stearate, and to compositions containing it. In accordance with the invention, erythromycin base is allowed to react with acetyl chloride in the presence of sodium hydrogen carbonate, by using ethyl acetate as the solvent. Further, from the erythromycin acetate ester thus obtained, stearate salt is further prepared without in between isolating the ester.

GB-patent No. 834,397 describes one method of preparing erythromycin acetate ester. In the reaction in question, the acylation reaction occurs in acetone, and the obtained ester is isolated by adding water to the reaction mixture. However, it has been observed in practice that acetate ester crystallizes out very poorly from an aqueous solution, for which reason the total yield of the reaction is quite modest. Furthermore, the product is difficult to filter, and it is not possible to remove the one molecule of water of crystallization present in the product without using very cumbersome procedures. If the product of the method in question were used for the preparation of stearate salt, the preparation and isolation of the stearate would be very difficult.

In accordance with the present invention, an acetate ester is prepared in which the acetyl group is in the 2' position, first in ethyl acetate, whereafter the obtained ester is dried azeotropically by distilling off part of the ethyl acetate. A directly equivalent amount of stearic acid is added to the mixture thus obtained. The stearate salt is isolated from the solution by distilling off part of the ethyl acetate (b.p. 76°-77° C. and by replacing it at the same time with petroleum ether, which has a higher boiling point (b.p. 120° C.). The solution is cooled slowly to room temperature and further to 0° C., the solution is distilled, and the obtained salt is washed and dried. The yield by this procedure is quite high, about 90%.

It has been observed that about 40° C. is the most advantageous temperature for the preparation of erythromycin acetate ester. Lowering of the temperature causes precipitation, and raising of the temperature causes at least some degree of hydrolysis.

Ethyl acetate has proved to be the most practicable of the solvents. Chlorinated hydrocarbons and toluene are also suitable for the purpose, although not as good as ethyl acetate. For the isolation of the salt it is advantageous to select a solvent which has a boiling point above 100° C., because with its aid it is easy to remove from the solution both all the water and also the previously used solvent, such as ethyl acetate.

The earth alkali or alkali metal carbonate or hydrogen carbonate used is, owing to its weak base properties, a suitable acid acceptor.

Erythromycin preparations currently on the market include erythromycin base, erythromycin lactobionate, erythromycin stearate (salt) and erythromycin estolate, which is the lauryl sulfate salt of the propionyl ester of erythromycin. The stearate salt is absorbed poorly. The absorption further decreases if the patient eats close to the time of taking the medicine or in connection with it.

The greatest disadvantage of the base-form preparations is that gastric acids convert them to ineffective compounds. The conversion can be avoided by making the tablets such that they do not dissolve until in the intestine. However, these so-called enterotablets are more expensive to manufacture than conventional ones, in addition to which their preparation involves a certain uncertainty in the respect that it is difficult to produce preparations which always dissolve in precisely the same way. This results in variation in the concentration of the active ingredient in the blood.

Erythromycin estolate is liver toxic. For this reason, of course, its use is avoided, whenever possible.

Using the erythromycin derivative according to the present invention the disadvantages of other erythromycin derivatives have been successfully avoided and a product has been achieved which need not be prepared into enterotablets or enterocapsules in order to ensure full effectiveness. Furthermore, the absorption of the compound is good, from which it follows that a smaller amount of the active ingredient than before suffices to produce in the blood a concentration for which a larger amount of the active ingredient was necessary previously. For this reason the tablets made from acetyl erythromycin stearate are smaller in size and therefore less unpleasant to take. Large tablets have, for example, had the disadvantage that they relatively often stick to the esophagus and may cause local injury.

The following tests illustrate the absorption and liver toxicity of erythromycin acetate stearate.

Absorption tests

In the absorption tests the absorption of erythromycin acetate stearate was compared with the absorption of erythromycin stearate salt in human subjects after fast and after a meal. Thus, the accompanying FIG. 1 depicts the result of the above-mentioned comparison test in subjects after fast, and FIG. 2 depicts the corresponding result in subjects who had had a standard breakfast.

As can be clearly seen from FIGS. 1 and 2, the absorption of acetyl erythromycin stearate is clearly better than the absorption of erythromycin stearate after fast, and furthermore, the difference is even clearer in the subjects who had a meal in connection with the taking of the medicine. The blood serum concentration of the medicine increased clearly faster when the compound according to the invention was used than when the reference compound was used, in addition to which the level rose three times higher than when using the reference compound. Furthermore, it can be seen from the figures that the concentration in the serum remained clearly higher than it did with the reference compound even after eight hours.

Intake of food together with the medicine lowers the maximum concentration in blood serum also with the compound according to the invention, but with erythromycin stearate the lowering is so great that the obtained level is not sufficient as a therapeutic dose.

Thus it has been clearly shown that the compound according to the invention is effectively absorbed irrespective of the conditions.

Liver toxicity experiments

In order to determine the liver toxicity of the stearate salt of erythromycin acetate ester, its action on enzymes describing liver function was compared with the action of certain other erythromycins on the same enzymes. The reference compounds used in the experiments were erythromycin stearate salt and erythromycin estolate. The experimental animals used were dogs, in whom the enzymes describing the function of the liver were determined both prior to and after the test period of five days. The results are given in Table 1.

As is clearly indicated by the values in the table, erythromycin estolate is clearly the most toxic of the compounds tested. The increase caused by it in the ASAT and ALAT values is clearly the greatest, in addition to which it is the only one of the compounds tested which caused an increase also in the APHOS and —GT values.

Pharmacological studies

To test the pharmacological activity of the new drug, acetyl erythromycin stearate, following procedure was followed.

Bacterial test culture

Diplococcus pneumoniae type 3 cultures were obtained from Helsinki University, Department of Serology and Bacteriology. The bacteria were transferred with a metal loop from the anaerobic culture medium into blood culture bottles of volume 50 ml (Hemobact, Orion Diagnostica, Espoo Finland). The bacteria were incubated at 37° C. for 24 hours yielding about $10^5$ bacteria/ml.

Test animals

White NMRI mice of both sexes weighing from 20 to 25 g.

Test procedure

Test mices were divided into 12 groups, each consisting of 10 mices. Erythromycin stearate and correspondingly acetyl erythromycin stearate were given to the animals which had been given 100 μl of the bacterial culture (about $10^5$ bacteria/ml) intraperitoneally by a subcutaneous way in the following manner:

| Erythromycin stearate group | | Acetyl erythromycin stearate | |
|---|---|---|---|
| (1) | 0 mg/kg (untreated | (7) | 0 mg/kg (untreated |
| (2) | 1,5 mg/kg control) | (8) | 1,5 mg/kg control) |
| (3) | 5 mg/kg | (9) | 5 mg/kg |
| (4) | 15 mg/kg | (10) | 15 mg/kg |
| (5) | 50 mg/kg | (11) | 50 mg/kg |
| (6) | 150 mg/kg | (12) | 150 mg/kg |

The drugs were suspended in 0,125% carboxymethylcellulose (CMC), pH was adjusted to 6 and the solution was kept in ice to minimize the rate of hydrolysis. The drugs were injected subcutaneously at 12 hours intervals.

Results

All of the control group animals died during 48 hours from infection. The treatment with erythromycin stearate and with acetyl erythromycin stearate protected the mice dose-dependently from death. None of the animals died when treated with acetyl erythromycin stearate with 150 mg/kg b.i.d. while 1/10 died when treated with erythromycin stearate with the same dose.

As can be seen above the pharmacological studies clearly show that acetyl erythromycin stearate has, given in a subcutaneous way, at least as good an activity as erythromycin stearate.

If given in an oral way the activity is even much better than that of erythromycin stearate because the absorption rate of acetyl erythromycin stearate is 2–4 times better than that of erythromycin stearate. This is due to the effect of gastric juice on erythromycin stearate.

The following examples illustrate the preparation of the stearate salt of erythromycin acetate and also the preparation of usable pharmaceutical compositions which contain acetyl erythromycin stearate as the active ingredient.

EXAMPLE 1

Preparation of erythromycin acetate stearate 200 g (2.38 mol) of sodium hydrogen carbonate was added to a solution which contained 400 g (0.545 mol) of erythromycin base in 3.6 liters of ethyl acetate. The obtained suspension was heated to 40° C., and 46.4 ml (0.65 mol) of acetyl chloride in 400 ml of ethyl acetate was added to it in the course of 2-3 hours. Stirring was continued after the adding for a further 2 hours of 40° C., whereafter 1 liter of water at 40° C. was added to it. The stirring was still continued for some time, whereafter the ethyl acetate layer was separated out, concentrated to 2.5 liters, and 155 g (0.545 mol) of stearic acid was added to it. The ethyl acetate was distilled off at normal pressure, and the leaving ethyl acetate was replaced with 2 liters of petroleum ether (b.p. 120° C.). The mixture was coolded slowly to room temperature and further to 0° C. The desired stearate salt was filtered out from the solution, washed with petroleum ether, and dried. The yield obtained was 520 g of product, 90% of the theoretical yield.

Analysis: $C_{57}H_{105}NO_{16}$ (mol. wt. 1060.42)
| Computed: | C = 64.56 | Obtained: | C = 64.74 |
| | H = 9.98 | | H = 10.21 |
| | N = 1.32 | | N = 1.28 |

EXAMPLE 2

Preparation of tablets

Using the compound according to the invention, a tablet having the following composition was prepared.

Acetyl erythromycin stearate corresponding to 250 mg of erythromycin—393 mg
Polyvinyl pyrrolidone—6 mg
Purified water*—54 mg
Microcrystalline cellulose—80 mg
Modified cellulose gum**(Ac-di-Sol ®)—10 mg
Mg stearate—2 mg
*Evaporates out from the process
**Croscarmellose sodium USP The active ingredient was granulated by means of an aqueous solution of polyvinyl pyrrolidone. The granules were dried and screened, whereafter the rest of the ingredients were mixed with the granules, and tablets were compressed from the obtained mass. The tablets were coated with a conventional pigment-cellulose film coating.

EXAMPLE 3

Preparation of tablets

Using the ingredients and quantities according to Example 2 but by leaving out the polyvinyl pyrrolidone and water, tablets were prepared as follows. The active ingredient and the microcrystalline cellulose, as well as the modified cellulose gum were mixed together. The powder mixture was dry granulated by compressing and screening, whereafter the Mg stearate was added and the mixture was compressed into tablets. A conventional film coating was also used.

EXAMPLE 4

Preparation of spherical granules

Acetyl erythromycin stearate corresponding to 125 mg of erythromycin—196.5 mg
Corn starch—50 mg
Granulated sugar—50 mg
Polyvinyl pyrrolidone—15 mg
Purified water*—
*Evaporates during the process The spherical granules were prepared using a Freund CF-360 granulator suitable for the purpose, in accordance with the operating instructions of the device.

TABLE 1

| | | \multicolumn{5}{c|}{TOXICITY TEST OF FIVE DAYS USING DOGS (n = 4)} |
|---|---|---|---|---|---|---|
| | | \multicolumn{5}{c|}{ACTIVITY OF LIVER ENZYMES ($\bar{n} \pm SD$)} |
| | | ALAT (mU/ml) | ASAT (mU/ml) | APHOS (mU/ml) | γ-GI (mU/ml) | Bilirubin (μmol/l) |
| Control | before | 30.5 ± 7.8 | 32.8 ± 7.0 | 227 ± 52.4 | 3.8 ± 2.9 | 15.0 ± 10.4 |
| | after | 30.0 ± 7.8 | 24.8 ± 1.7 | 234 ± 64.1 | 2.5 ± 1.7 | 7.5 ± 2.7 |
| Erythromycin stearate 278 mg/kg × 2 | before | 27.3 ± 6.85 | 25.5 ± 8.5 | 214 ± 48.3 | 3.0 ± 0.82 | 13.3 ± 5.7 |
| | after | 102.0 ± 48.0 | 33.3 ± 13.9 | 178 ± 38.7 | 3.3 ± 1.3 | 12.0 ± 4.1 |
| Erythromycin estolate 144 mg/kg × 2 | before | 24.0 ± 7.0 | 27.3 ± 6.4 | 218 ± 40.6 | 2.8 ± 1.3 | 10.0 ± 1.8 |
| | after | 285.8 ± 218.1 | 274.5 ± 233.8 | 610 ± 582.4 | 8.0 ± 5.7 | 11.5 ± 2.1 |
| Acetyl erythromycin stearate 145 mg/kg × 2 | before | 25.3 ± 3.9 | 29.0 ± 7.0 | 209 ± 39.7 | 2.5 ± 1.0 | 7.3 ± 1.0 |
| | after | 90.25 ± 51.15 | 24.5 ± 4.4 | 189 ± 40.6 | 3.3 ± 1.5 | 10.3 ± 3.4 |
| Acetyl erythromycin stearate 290 mg/kg × 2 | before | 26.5 ± 7.3 | 27.8 ± 9.2 | 180 ± 70.6 | 3.0 ± 0.0 | 13.0 ± 5.7 |
| | after | 177.0 ± 192.5 | 28.0 ± 50.9 | 197 ± 90.3 | 5.5 ± 4.4 | 8.8 ± 4.4 |

What is claimed is:

1. An antibiotic compound, acetyl erythromycin stearate, having the formula I

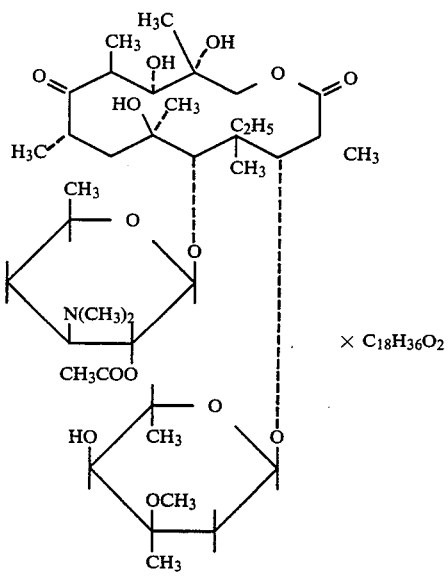

2. An antibiotic composition, comprising about 196.5 mg to about 393 mg acetyl erythromycin stearate as well as one or more ingredients selected from the group: liquid or solid carriers, fillers, lubricants and other ancillary or additive ingredients.

3. An antibiotic composition according to claim 2, comprising one or several ingredients selected from the group: polyvinyl pyrrolidone, microcrystalline cellulose, modified cellulose gum, corn starch, granulated sugar and magnesium stearate.

* * * * *